United States Patent
Tetzlaff et al.

(10) Patent No.: US 12,411,107 B2
(45) Date of Patent: Sep. 9, 2025

(54) GAS MEASURING DEVICE WITH HEATING MEANS

(71) Applicant: Wagner Group GmbH, Langenhagen (DE)

(72) Inventors: Uwe Tetzlaff, Neustadt (DE); Andre Heptner, Hannover (DE)

(73) Assignee: Wagner Group GmbH (DE)

( * ) Notice: Subject to any disclaimer, the term of this patent is extended or adjusted under 35 U.S.C. 154(b) by 894 days.

(21) Appl. No.: 17/628,328

(22) PCT Filed: Jul. 28, 2020

(86) PCT No.: PCT/EP2020/071246
§ 371 (c)(1),
(2) Date: Jun. 15, 2022

(87) PCT Pub. No.: WO2021/018881
PCT Pub. Date: Feb. 4, 2021

(65) Prior Publication Data
US 2022/0326178 A1   Oct. 13, 2022

(30) Foreign Application Priority Data
Jul. 31, 2019 (DE) ..................... 10 2019 120 699.5

(51) Int. Cl.
G01N 27/416 (2006.01)
G01N 1/44 (2006.01)
G01N 33/00 (2006.01)

(52) U.S. Cl.
CPC ........... *G01N 27/4163* (2013.01); *G01N 1/44* (2013.01); *G01N 33/0036* (2013.01)

(58) Field of Classification Search
CPC ........... G01N 33/0016; G01N 33/0004; G01N 33/0009; G01N 33/0011; G01N 33/0027;
(Continued)

(56) References Cited

U.S. PATENT DOCUMENTS

2004/0083793 A1   5/2004   Susko
2009/0141769 A1   6/2009   Baldwin et al.
(Continued)

FOREIGN PATENT DOCUMENTS

DE    102007058565 A1    6/2009
WO    WO-2014187689 A1 * 11/2014 ........... G01N 1/2247
(Continued)

OTHER PUBLICATIONS

English Machine Translation of WO2016175440 (Year: 2016).*
English machine Translation of WO2018053655 (Year: 2018).*

*Primary Examiner* — Gurpreet Kaur
(74) *Attorney, Agent, or Firm* — Frank H. Foster; Kremblas & Foster (57) ABSTRACT

A gas measuring device (100) for analyzing a gas mixture (310) and monitoring an environment (300) has a housing (110) for delimiting a measurement interior volume (120) and/or for separating the measurement interior volume (120) from the environment (300) containing the gas mixture (310). The housing has a gas inlet (111) and a gas outlet (112) for respective fluid-conducting connection between the measurement interior volume (120) and the environment (300), and an electrochemical gas sensor unit, which is arranged within the measurement interior volume (120), and which serves for determining a concentration of a gas fraction, in particular an oxygen fraction, contained in the gas mixture (310).

The gas measuring device (100) has a heating element (220) and with an open-loop and/or closed-loop control system (230) to increase or maintain an interior temperature ($T_I$) of the measurement interior volume (120) and settable by means of the control system (230).

16 Claims, 5 Drawing Sheets

(58) Field of Classification Search
CPC ........... G01N 33/0036; G01N 27/4163; G01N 27/26; G01N 27/416; G01N 1/44; G01N 1/28

See application file for complete search history.

(56) References Cited

U.S. PATENT DOCUMENTS

2017/0010207 A1    1/2017  Fetzner et al.
2018/0313800 A1*  11/2018  Rogers ............... G01N 33/0016
2020/0393432 A1*  12/2020  Swanson ............. G01N 27/404

FOREIGN PATENT DOCUMENTS

WO    WO-2016175440 A1 *  11/2016   ............... G01N 1/22
WO    WO-2018053655 A1 *   3/2018   ........... G01N 27/125

* cited by examiner

GAS MEASURING DEVICE WITH HEATING MEANS

BACKGROUND OF THE INVENTION

The invention relates to a gas measuring device for analyzing a gas mixture and for monitoring an environment, having a housing for delimiting a measurement interior volume and/or for separating the measurement interior volume from the environment containing the gas mixture, having a gas inlet and a gas outlet for respective fluid-conducting connection between the measurement interior volume and the environment, and a gas sensor unit, in particular electrochemical gas sensor unit, which is arranged within the measurement interior volume, for determining a concentration of a gas fraction, in particular an oxygen fraction, contained in the gas mixture.

The invention also relates to a heating means for such a gas measuring device and furthermore to a method for open-loop and/or closed-loop control of a heating means.

In the technical field of room and building monitoring, it is conventional, for example, to use gas measuring apparatuses for monitoring an environment and for analyzing a gas mixture, normally air, present in the environment. Such gas measuring apparatuses are advantageously accommodated in a housing, the gas inlet and gas outlet of which are in continuous fluid-conducting connection with the environment to be monitored. The actual gas sensor or the gas sensor unit is arranged within the housing in a measurement interior volume often also referred to as measurement cell. The term "measurement interior volume" is always understood to mean an interior volume of a gas measuring apparatus or of a gas measuring device, which contains the gas sensor unit. The housing delimits this measurement interior volume and can optionally also be used for separation from the environment. Also known are designs of gas measuring apparatuses with two housings, wherein an "interior" housing is provided for delimiting the measurement interior volume and an "exterior" housing is provided for separation with respect to the environment. For example, by installing the gas measuring apparatus upright in a room to be monitored, wherein the gas inlet is arranged under the gas outlet, due to free convection a continuous flow though the measurement interior volume and consequently a continuous analysis of the gas mixture and continuous monitoring of the environment can be achieved.

In the field of fire protection, gas measuring apparatuses are also used. Thus, gas measuring apparatuses are known in particular in connection with so-called oxygen reduction installations which lower the oxygen content within an environment, a so-called protected zone, to a level which is below the usual oxygen content in the ambient air and in particular below the ignition limit of materials present in the protected zone. However, preferably, sufficient oxygen should still remain in the environment, so that persons can linger in the protected zone. In order to exclude risk to these persons, gas measuring apparatuses in the form of oxygen measuring apparatuses for monitoring the environment are installed in the corresponding protected zone. These oxygen measuring apparatuses comprise oxygen sensors such as, for example, paramagnetic oxygen sensors, zirconium dioxide oxygen sensors or also electrical oxygen sensors for determining the volume-related oxygen content in the ambient air. Often, oxygen sensors have a temperature-dependent measurement behavior, that is to say the ambient temperature influences the measurement accuracy. For example, the measurement deviation of a commercial electrochemical oxygen sensor increases by approximately −2 volume % at an ambient temperature of −20° C. with respect to an ambient temperature of +20° C., i.e., the electrochemical oxygen sensor indicates a value for the oxygen volume fraction of the same gas mixture at an ambient temperature of −20° C. that is 10% lower than at an ambient temperature of +20° C. A reliable use of temperature-dependent oxygen sensors for monitoring rooms or protected zones with low temperatures (for example, frozen storage facilities with ambient temperatures of −30° C.) is therefore not possible.

From other technical fields in which gas sensors are used, it is known to control the temperature of a gas mixture flow supplied to the gas sensor. From WO 2016/083576 A2, for example, a device or spectrometer for detection of gases in breathing air by isotope separation techniques is disclosed. The spectrometer comprises a laser detector arrangement with a laser light source and a detector as well as a measurement cell located in a beam path between laser light source and detector, having an inlet and an outlet for the breathing air to be analyzed. For the analysis of the breathing air, a patient breathes into the gas inlet of the device, as a result of which the breathing air to be analyzed arrives discontinuously, intermittently in the measurement cell. To improve the measurement result, a preliminary temperature control unit for flow-dependent preheating is provided, which should allow an even heating and drying of the cyclically arriving breathing air of the patient. The preliminary temperature control unit comprises a measurement resistor, a preheating element and a pre-heating element controller, which are connected to one another in the manner of a control loop. The volume flow of the breathing air is computed by means of a signal obtained from the measurement resistor and used via a control unit for the preheating element for flow-dependent closed-loop control of the heating of the breathing air. A disadvantage of the flow-dependent closed-loop control is that the breathing air arrives cyclically, intermittently, as a result of which a closed-loop control which is rapid or high-frequency and therefore prone to failure is also necessary. The temperature in the measurement cell itself is also controlled by means of a main temperature control unit, wherein the control variable for the main temperature controller is measured at the bottom of the measurement cell by a temperature sensor. For the main temperature closed-loop control, it is thus necessary to integrate an additional temperature sensor in the measurement cell, whereby, on the one hand, influencing the measurement result can result, and, on the other hand, conversion of the measurement cell is necessary.

SUMMARY OF THE INVENTION

The problem addressed by the present invention is to eliminate the disadvantages of the prior art and to create a gas measuring device which allows the greatest possible measurement accuracy independently of the temperature of the gas mixture to be measured and/or of the ambient temperature.

The problem is solved by a gas measuring device according to the invention having a heating means according to claim 1, a heating means according to the invention for a gas measuring device according to claim 11, and a method according to the invention for open-loop and/or closed-loop control of a heating means according to claim 12.

A gas measuring device according to the invention of the type designated in further detail at the start is characterized by a heating means having at least one heating element and an open-loop and/or closed-loop control system, wherein, to increase or to maintain an interior temperature ($T_I$) of the measurement interior volume, a heating temperature ($T_H$) of the at least one heating element is settable by means of the open-loop and/or closed-loop control system.

In the sense of the invention, it is thus provided to enhance the gas measuring device by means of a heating means which enables the setting of a desired interior temperature ($T_I$) in the measurement interior volume, i.e., where the gas sensor unit is arranged, preferably in the immediate environment of the gas sensor unit. For example, it is also conceivable to arrange the gas sensor unit within the gas inlet or the gas outlet, or in regions or components of the gas measuring device and/or of the heating means through which the gas mixture flows. For setting the interior temperature ($T_I$), said interior temperature is first increased to a desired temperature range, for example, to a range between 0° C. and 20° C. or to a desired temperature value, for example, 10° C., and subsequently maintained there. Thereby, the determination of the concentration of a gas fraction contained in the gas mixture to be analyzed, in particular of an oxygen fraction, is enabled under constant temperature conditions within the measurement interior volume and therefore independently of the ambient temperature ($T_U$) of the environment within which the gas measuring device is arranged. The heating temperature ($T_H$) of the at least one heating element is settable by means of an open-loop and/or closed-loop control system which, in the simplest design, has an operating element such as a rotary switch, which can be actuated manually by a user.

In particular for gas measuring devices for continuous room monitoring with open design, in which the measurement interior volume and the gas sensor unit are in continuous exchange with the ambient air via a gas inlet and a gas outlet, a substantially broader field of use is opened by the uncoupling according to the invention of the ambient temperature ($T_U$) from the interior temperature ($T_I$) of the measurement interior volume. The gas measuring device according to the invention can consequently also be used at particularly low ambient temperatures ($T_U$) of, for example, −30° C., within frozen storage facilities, wherein a reliable monitoring of the concentration of a gas fraction, in particular of the oxygen fraction, is ensured. At the same time, the useful life of the gas sensor, in particular of the oxygen sensor, can be increased by the operation at positive temperatures.

In addition, the invention also relates to designs of gas measuring devices in which the gas inlet and the gas outlet are designed as an identical component and/or as the same opening or recess, wherein the gas mixture then enters or is let into the housing and also again exits or is let out of the housing through the combined gas inlet and outlet.

In an advantageous design, one or more heating elements are arranged within the housing in the measurement interior volume of the gas measuring device or they can be integrated in the housing itself, for example, in the cover thereof. In order to reduce the heat energy necessary for increasing or for maintaining the temperature or the heating power to be applied, the measurement interior volume can be insulated with respect to the environment. Here, it is conceivable to provide with insulation only a portion of the measurement interior volume, within which the gas sensor unit and/or the at least one heating element is/are arranged. In terms of construction, it is simpler to equip the entire housing of the gas measuring device with insulation and/or design it so that it is insulating.

A particularly high operational reliability is achieved in that the heating means, according to an advantageous embodiment, has a greater number of heating elements than would be necessary for the total heat energy or heating power necessary for increasing or maintaining the desired interior temperature ($T_I$) of the measurement interior volume. Thus, in the case of a failure of one or more heating elements, the total necessary heating power can moreover be provided by additional, in particular redundant, heating elements.

Advantageously, the at least one heating element according to an embodiment of the invention can comprise a heating resistor on a radiator, wherein the heating temperature ($T_H$) of the heating element can be open-loop controlled by means of a heating voltage applied to the heating resistor.

For this purpose, the heating resistor is thermally coupled to the radiator, wherein heat energy is generated in the heating resistor, in that a current flows through said heating resistor. The resulting heating temperature ($T_H$) at the heating element, in particular at the radiator, is open-loop controlled depending on the heating voltage applied to the heating resistor.

In order to obtain feedback on the instantaneous heating temperature ($T_{H, Actual}$) actually prevailing on the heating element, according to a likewise advantageous variant of the invention, the open-loop and/or closed-loop control system can have at least one first temperature sensor for measuring the instantaneous heating temperature ($T_{H, Actual}$) of the at least one heating element and can be designed for the open-loop and/or closed-loop control of the instantaneous heating temperature ($T_{H, Actual}$) on the basis of a presettable target heating temperature ($T_{H, Target}$) of the at least one heating element.

By an optional first temperature sensor, designed in particular as a measuring resistor (for example, Pt100), on the heating element, by means of the open-loop and/or closed-loop control system, a target value/actual value comparison of the actually prevailing instantaneous heating temperature ($T_{H, Actual}$) with a presettable and/or preset target heating temperature ($T_{H, Target}$) can thus be carried out, and, based on the temperature deviation of the instantaneous heating temperature (actual value), closed-loop control from the preset target heating temperature (target value), a closed-loop control can be carried out.

The presettable and/or preset target heating temperature ($T_{H, Target}$) can, for example, be manually set as desired or can be stored as a fixed value in the open-loop and/or closed-loop control system. According to a development of the above variant of the invention, it is advantageous if the open-loop and/or closed-loop control system has at least one second temperature sensor for measuring a gas inlet temperature ($T_G$) of the gas mixture present at the gas inlet and/or an ambient temperature ($T_U$) of the gas mixture present in the environment, and the presettable target heating temperature ($T_{H, Target}$) can be determined based on a correlation or another relationship, stored in the open-loop and/or closed-loop control system, between the interior temperature ($T_I$) of the measurement interior volume and the instantaneous heating temperature ($T_{H, Actual}$) of the at least one heating element, depending on the measured gas inlet temperature ($T_G$) and/or the measured ambient temperature ($T_U$).

Thus, preferably, the presettable target heating temperature ($T_{H, Target}$) is computed as function $f(T_G; T_U)$ of the gas inlet temperature ($T_G$) measured by means of the second temperature sensor and/or of the measured ambient temperature ($T_U$) by the open-loop and/or closed-loop control system. By closed-loop control of the heating temperature ($T_H$) of the at least one heating element, i.e., comparison of the instantaneous heating temperature ($T_{H, Actual}$) with the computed target heating temperature ($T_{H, Target}$) and actuation by means of a heating voltage, an indirect open-loop and/or closed-loop control of the interior temperature ($T_I$) of the measurement interior volume is thus possible, interior temperature ($T_I$) which then functions as (indirect) reference variable. The interior temperature ($T_I$) resulting in each case when the corresponding instantaneous heating temperature ($T_{H, Actual}$) (actual value=target value) has been reached in the measurement interior volume of the gas measuring device, based on a correlation or based on another relationship, in particular a functional relationship, between the interior temperature ($T_I$) of the measurement interior volume and the instantaneous heating temperature ($T_{H, Actual}$) of the at least one heating element, is stored in the open-loop and/or closed-loop control system. For example, a proportionality between the interior temperature ($T_I$) and the instantaneous heating temperature ($T_{H, Actual}$) can exist and be stored as function.

In particular in the form of table-based association but also based on an association, stored in the open-loop and/or closed-loop control system, of concrete values of the instantaneous heating temperature ($T_{H, Actual}$) with corresponding values of the interior temperature ($T_I$), alternatively or optionally, the presettable target heating temperature ($T_{H, Target}$) can be determined depending on the measured gas inlet temperature ($T_G$) and/or the measured ambient temperature ($T_U$).

Here, it is moreover advantageous that the gas measuring device is designed with constant preset geometric ratios and/or other parameters. For example, the measurement interior volume of the gas measuring device, the distance between the at least one heating element and the gas sensor unit, the (respective) heating power or the total heating power of the at least one heating element, the placement of the temperature sensors, the degree of insulation and/or the other design of the gas measuring device can be firmly preset. The flow rate, generated in particular by free or forced convection, at which the gas mixture flows through the measurement interior volume, is set to be constant, so that the interior temperature ($T_I$) depends only on the gas inlet temperature ($T_G$) measured at the gas inlet and on the instantaneous heating temperature ($T_{H, Actual}$) measured at the heating element. A correlation or another relationship between the interior temperature ($T_I$) and the instantaneous heating temperature ($T_{H, Actual}$) and/or an association of concrete values of the instantaneous heating temperature ($T_{H, Actual}$) with corresponding values of the interior temperature ($T_I$) is then experimentally determined for different gas temperatures ($T_G$) and stored in the open-loop and/or closed-loop control system.

Due to the indirect closed-loop control, it is thus possible to dispense with a temperature sensor in the measurement interior volume and/or on the gas sensor unit, whereby a mutual electrical influence is ruled out, and at the same time, the modifications and/or conversions to be carried out on the gas measuring device are minimized. As desired, instead of the gas inlet temperature ($T_G$) or in addition to said gas inlet temperature, the ambient temperature ($T_U$) can be used for computing the target heating temperature ($T_{H, Target}$)

In the practical application of this variant of the invention, it is thus advantageous to provide gas measuring devices with an always similar or even identical design in order to implement a non-error-prone and reliable (indirect) open-loop and/or closed-loop control of the interior temperature ($T_I$) of the measurement interior volume based on the respective measured gas inlet temperature ($T_G$) and/or the ambient temperature ($T_U$).

In an advantageous development, the open-loop and/or closed-loop control system of the heating means comprises a digital computation unit, in particular a digital microcontroller, which has interfaces with the at least one first temperature sensor, the at least one second temperature sensor and the at least one heating element, and wherein the correlation or the other relationship between the interior temperature ($T_I$) of the measurement interior volume and the instantaneous heating temperature ($T_{H, Actual}$) of the at least one heating element and/or the association of concrete values of the instantaneous heating temperature ($T_{H, Actual}$) with corresponding values of the interior temperature ($T_I$) is stored in the computation unit, and the computation unit is designed for determining the presettable target heating temperature ($T_{H, Target}$) depending on the measured gas inlet temperature ($T_G$) and/or the measured ambient temperature ($T_U$).

Preferably, the computation of the required target heating temperature ($T_{H, Target}$) as well as the closed-loop control of the instantaneous heating temperature ($T_{H, Actual}$) is carried out by the digital computation unit. For this purpose, in the computation unit, in particular on a storage unit, for example, in the form of programming and/or software, the desired interior temperature ($T_I$) or a desired range of the interior temperature ($T_I$) of the measurement interior volume is or can be stored. In addition, the correlation or the other relationship between the interior temperature ($T_I$) and the instantaneous heating temperature ($T_{H, Actual}$) and/or an association of concrete values of the instantaneous heating temperature ($T_{H, Actual}$) with corresponding values of the interior temperature ($T_I$) is also stored. On the input side, between the respective analog measuring temperature sensors and the digital computation unit, by means of a suitable analog-digital converter, a conversion of the analog sensor signal is carried out. On the output side, the digital signal of the digital computation unit is converted, wherein the heating resistor of the heating element is actuated by the computation unit via a pulse width modulation or a switching power supply by means of an analog heating voltage.

In a development, the computation unit is advantageously designed to output an error message and/or to switch off the heating means if a measured value of the instantaneous heating temperature ($T_{H, Actual}$) is less than a temperature minimum reference value stored in the computation unit or if the measured value of the instantaneous heating temperature ($T_{H, Actual}$) is greater than a stored temperature maximum reference value.

For example, an undershooting of the stored temperature minimum reference value by the instantaneous heating temperature ($T_{H, Actual}$) can indicate a defect or failure of one or more heating elements, in this case, an error message is preferably output by the computation unit. Optionally, in a corresponding manner, the gas inlet temperature ($T_G$) and/or the ambient temperature ($T_U$) can also be monitored, wherein the output of an error message then occurs if a stored minimum ambient temperature has been undershot by the measured value and, for example, the total heating power of the heating means is not sufficient for increasing or maintaining the desired interior temperature.

A switching off of the heating means is preferably carried out if a measured value of the instantaneous heating temperature ($T_{H, Actual}$) is greater than a stored temperature maximum reference value, for example, 50° C.-60° C., i.e., if there is a risk of overheating and of an associated defect or failure of one or more heating elements.

To switch off the heating means, a fault relay can be provided in the open-loop and/or closed-loop control system, wherein the computation unit comprises a comparator function from which the fault relay is actuated. Redundantly to this software-actuated switching off, with the same fault relay, a hardware-actuated switching off can also be implemented, wherein, for this purpose, a corresponding component such as a comparator or a bimetal is incorporated in a circuit actuating the fault relay.

In a preferred design, the gas measuring device comprises a gas mixture return with a gas mixture return line, wherein a gas mixture flowing out at the gas outlet of the housing can at least partially be supplied to the heating means via the gas mixture return line.

By returning the already preheated gas mixture, the heating power demand of the at least one heating element can be reduced. At the gas inlet, the returned fraction of the gas mixture, together with a fraction of the gas mixture coming from the environment, can be supplied to the measurement interior volume.

According to an advantageous variant of the invention, the heating means has a fan for generating a gas mixture flow.

In a development of this variant of the invention, the increasing or the maintaining of the interior temperature ($T_I$) of the measurement interior volume of the gas measuring device can be carried out indirectly by heating the gas mixture flow by the at least one heating element.

Preferably, the fan is set at a constant rotational speed for generating a constant volume flow, so that changes in the volume flow of the gas mixture flow do not have to be taken into consideration for the open-loop and/or closed-loop control of the heating power or of the instantaneous heating temperature ($T_{H, Actual}$). In that the gas mixture flow is indirectly used in order to increase or maintain the interior temperature ($T_I$) of the measurement interior volume, a variable arrangement of the at least one heating element, for example, outside of the housing of the gas measuring device, in particular also within the gas mixture return line, is enabled. Advantageously, the fan and/or the at least one heating element are arranged, with respect to the gas mixture flow direction, before the gas sensor unit. Thereby, the modifications or conversions necessary for the gas measuring device itself can be further minimized.

Precisely for conversion of gas measuring devices which are already in operation, it is particularly advantageous according to an embodiment that the heating means has a heater housing for accommodating the at least one heating element and for accommodating the open-loop and/or closed-loop control system, with a heater housing inlet for fluid-conducting connection with the environment and a heater housing outlet for fluid-conducting connection with the gas inlet of the housing of the gas measuring device.

A heater housing accommodating the heating means can thus be implemented separately from the housing of the gas measuring device, wherein the heater housing outlet is connected directly or indirectly by means of a connection element, such as an insulated plastic pipe, to the gas inlet of the housing of the gas measuring device.

Within the heater housing, a fan for generating a gas mixture flow can also optionally be accommodated; a second temperature sensor for measuring the gas inlet temperature ($T_G$) of the gas mixture present at the gas inlet and/or of the ambient temperature ($T_U$) of the gas mixture present in the environment is preferably arranged on the heater housing inlet.

In connection with the closed-loop control concept explained above, in this embodiment, due to the separate heater housing and the indirect open-loop and/or closed-loop control of the interior temperature ($T_I$) of the measurement interior volume, the heating means can be implemented as completely separate spatially and electrically from the gas sensor unit. Modifications of the gas measuring device, in particular in the measurement interior volume, are thus completely avoided. A negative effect on the measurement accuracy of the gas sensor unit due to electrical influences of the heating device can be prevented by potential separation and/or galvanic separation. The heating means can thus be converted as a stand-alone operating module for the open-loop and/or closed-loop control of the interior temperature ($T_I$) of the measurement interior volume of a gas measuring device.

The problem of the invention set at the start is therefore also solved by a heating means for a gas measuring device, in particular for a gas measuring device according to one of the above described embodiments, for increasing or maintaining an interior temperature ($T_I$) of a measurement interior volume of the gas measuring device, having a heater housing with a heater housing inlet for fluid-conducting connection with an environment containing a gas mixture and a heater housing outlet for fluid-conducting connection with the measurement interior volume of the gas measuring device. Said heating means moreover having at least one heating element which is arranged within the heater housing and an open-loop and/or closed-loop control system which is arranged within the heater housing and designed for setting a heating temperature ($T_H$) of the at least one heating element.

According to the invention, the open-loop and/or closed-loop control system has at least one first temperature sensor for measuring an instantaneous heating temperature ($T_{H, Actual}$) of the at least one heating element and is designed for open-loop and/or closed-loop control of the instantaneous heating temperature ($T_{H, Actual}$) on the basis of a presettable target heating temperature ($T_{H, Target}$) of the at least one heating element. The open-loop and/or closed-loop control system moreover has at least one second temperature sensor for measuring a gas inlet temperature ($T_G$) of the heater housing inlet and/or an ambient temperature ($T_U$) of the gas mixture present in the environment, and the presettable target heating temperature ($T_{H, Target}$), can be determined on the basis of a correlation and/or another relationship, stored in the open-loop and/or closed-loop control system, between the interior temperature ($T_I$) of the measurement interior volume and the instantaneous heating temperature ($T_{H, Actual}$) of the at least one heating element and/or on the basis of an association, stored in the open-loop and/or closed-loop control system, of concrete values of the instantaneous heating temperature ($T_{H, Actual}$) with corresponding values of the interior temperature ($T_I$), in each case depending on the measured gas inlet temperature ($T_G$) and/or the ambient temperature ($T_U$).

Finally, the problem of the invention is also solved by a method for open-loop and/or closed-loop control of a heating means with at least one heating element for a gas measuring device, in particular for a gas measuring device according to one of the above embodiments with a heating means according to the invention, wherein the method has the following steps:

Acquiring a gas inlet temperature ($T_G$) and/or an ambient temperature ($T_U$), which is measured by means of a first temperature sensor. Acquiring an instantaneous heating temperature ($T_{H, Actual}$) of the at least one heating element, which is measured by means of a second temperature sensor. Computing a target heating temperature ($T_{H, Target}$) for the heating element depending on the measured gas inlet temperature ($T_G$) and/or the measured ambient temperature ($T_U$). Open-loop and/or closed-loop controlling of the instantaneous heating temperature ($T_{H, Actual}$) based on the computed target heating temperature ($T_{H, Target}$).

According to an advantageous method variant, by means of the instantaneous heating temperature ($T_{H, Actual}$), the interior temperature ($T_I$) of a measurement interior volume of the gas measuring device is open-loop controlled, wherein the computation of the target heating temperature ($T_{H, Target}$) for the heating element occurs based on a correlation or another relationship between the interior temperature ($T_I$) and the instantaneous heating temperature ($T_{H, Actual}$) and/or based on an association of concrete values of the instantaneous heating temperature ($T_{H, Actual}$) with corresponding values of the interior temperature ($T_I$).

BRIEF DESCRIPTION OF THE SEVERAL VIEWS OF THE DRAWINGS

Other details, features, feature (sub)combinations, advantages and effects on the basis of the invention result from the following description of the preferred embodiment examples of the invention and the drawings. The drawings show, in FIG. 1 a diagrammatic representation of the first exemplary embodiment of a gas measuring device according to the invention with integrated heating means, FIG. 2 a diagrammatic representation of the second exemplary embodiment of a gas measuring device according to the invention with upstream heating means, FIG. 3 a diagrammatic representation of a third exemplary embodiment of a gas measuring device according to the invention with upstream heating means and gas mixture return, FIG. 4 a block diagram of an exemplary control loop of a closed-loop and/or open-loop control system of a heating means according to the invention, and FIG. 5 a flow chart of an exemplary sequence of a method according to the invention for open-loop and/or closed-loop control of a heating means for a gas measuring device.

The figures are only of exemplary nature and used only for the understanding of the invention. The same elements are provided with the same reference numerals.

DETAILED DESCRIPTION OF THE INVENTION

Figure 1:
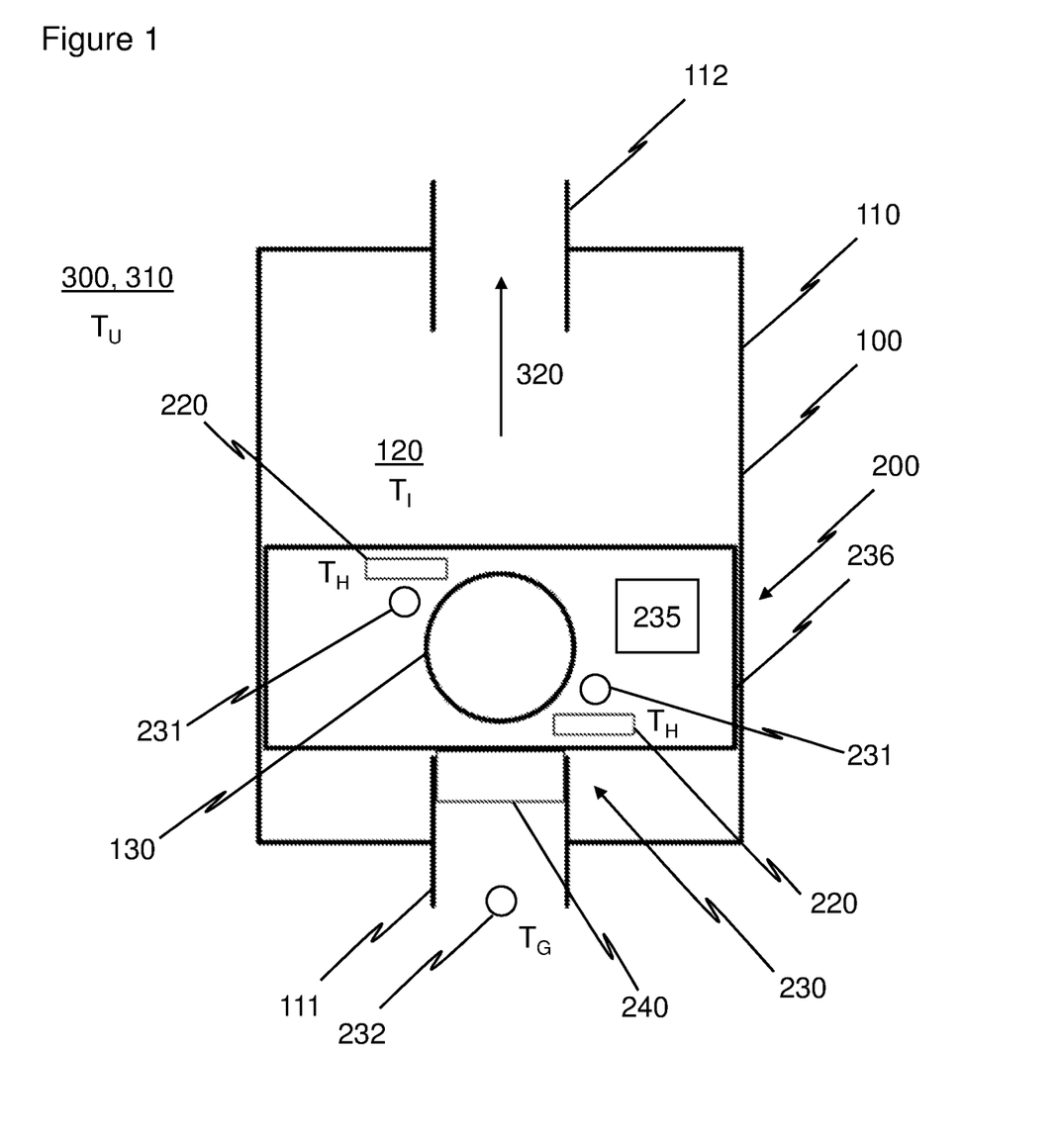

In FIG. 1, a first exemplary embodiment of a gas measuring device 100 according to the invention with integrated heating means 200 is diagrammatically represented. The gas measuring device 100 comprises a housing 110 which separates a measurement interior volume 120 from an environment 300. Here, a gas inlet 111 and a gas outlet 112 are formed on mutually facing housing walls and in each case are provided for fluid-conducting connection with the environment 300. The environment 300 can be, for example, a protected zone of an oxygen reduction installation, within which a reduction of the oxygen content is carried out by introducing an inert gas. For monitoring this environment 300, by means of the gas measuring device 100, an analysis, in particular a continuous analysis, of a gas mixture 310, for example, of oxygen-reduced ambient air, present in the environment 300 can be carried out.

Advantageously, for this purpose, within the measurement interior volume 120 of the gas measuring device 100, a gas sensor unit 130 is placed, which, for the analysis of the gas mixture 310, determines the concentration of a gas fraction in particular an oxygen fraction, contained in the gas mixture 310. In an advantageous design, the gas sensor unit 130 is a commercial electrochemical oxygen sensor. The gas measuring device 100 can be placed within the environment 300 to be monitored, wherein a continuous exchange of the gas mixture 310 between the measurement interior volume 120 and the environment 300 occurs due to a gas mixture flow 320, generated, for example, by free convection, from the gas inlet 111 to the gas outlet 112. Alternatively and not shown in this figure, it is also conceivable to design the gas inlet 111 and the gas outlet 112 as an identical component and/or on the same housing wall, in that, for example, a pipe connection or a recess of the housing, protected by a grate, functions as gas inlet and outlet 111, 112. The gas mixture 310 is then let in or let out through the same opening or recess functioning as gas inlet and outlet 111, 112, wherein the gas mixture flow 320 then enters the housing 110 at the gas inlet and outlet 111, 112, passes through the gas sensor unit 130 and subsequently exits again from the gas inlet and outlet 111, 112.

In order to be able to determine the gas fraction contained in the gas mixture 310 being influenced by the ambient temperature $T_U$, a heating means 200 is provided here as component of the gas measuring device 100. The heating means 200 in this embodiment comprises, for example, two heating elements 220 as well as an open-loop and/or closed-loop control system 230 with a digital computation unit 235, in particular a digital microcontroller, which is connected to a printed circuit board 236. Alternatively, it is also conceivable to integrate the heating elements 220 in a cover of the housing 110. The digital computation unit 235 is connected on the input side via interfaces to at least a first temperature sensor 231, in the present case to two first temperature sensors 231, for measuring an instantaneous heating temperature $T_{H, Actual}$ of the heating elements 220 and to at least one second temperature sensor 232 for measuring a gas inlet temperature $T_G$ present at the gas inlet 111 and/or an ambient temperature $T_U$ of the gas mixture 310 present in the environment 300. In the present embodiment example, the gas inlet temperature $T_G$ corresponds to the ambient temperature $T_U$. On the output side, via corresponding interfaces of the computation unit 235, the heating elements 220 are actuated. Each heating element 220 has in particular a heating resistor 221 (see FIG. 4) and a radiator (not represented), which are thermally coupled to one another. By means of the heating elements 220, the interior temperature $T_I$ of the measurement interior volume 120 can be increased and/or maintained at a desired temperature level. By means of an optional fan 240, by forced convection, a gas mixture flow 320 can be generated, the flow rate of which and/or volume flow of which can be set or controlled based on the rotational speed of the fan 240.

Figure 2:
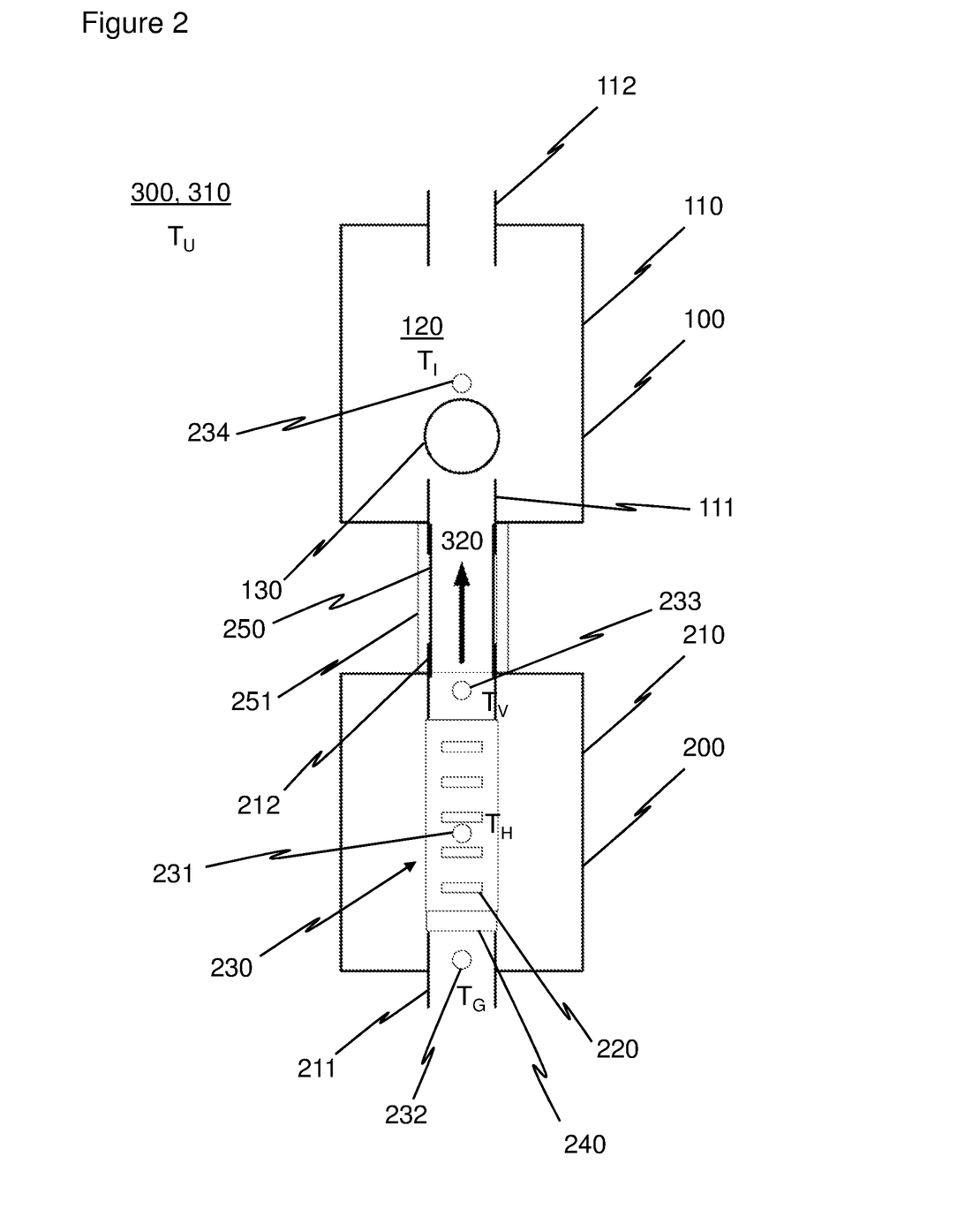

A second exemplary embodiment of a gas measuring device 100 is diagrammatically represented in FIG. 2 and essentially has components which correspond to the components of the first exemplary embodiment, wherefore they are also not explained in greater detail again. However, unlike the first exemplary embodiment, the heating means 200 here is designed with its own separately implemented heater housing 210, the heater housing inlet 211 of which leads in a fluid-conducting manner into the environment 300, and the heater housing outlet 212 of which, here, for example, via a pipe connection 250, in particular via a plastic pipe provided with insulation 251, is connected to the gas inlet 111 of the housing 110 of the gas measuring device 100. Accommodated in the heater housing 210 are five heating elements 220 in total, which are actuated by the digital computation unit 235, not represented here, the open-loop and/or closed-loop control system 230 as well as a first temperature sensor 231 and a second temperature sensor 232. The second temperature sensor 232 for measuring the non-preheated gas inlet temperature $T_G$ or ambient temperature $T_U$ in this embodiment is arranged on the heater housing inlet 211. Also, within the heater housing 210, a fan 240 for generating a gas mixture flow 320 is provided. The gas mixture flow 320 is preheated here already in the heater housing 210, with regard to the flow direction of the gas mixture flow 320, upstream of the gas measuring device 100, by means of the heating elements 220. Here, an indirect increasing and/or an indirect maintaining of the interior temperature $T_I$ is implemented at the gas sensor unit 130. Optionally, the heating means 200 moreover comprises a third temperature sensor 233 which is arranged on the heater housing outlet 212, downstream of the heating elements 220, for measuring a preheating temperature $T_V$ of the already heated gas mixture flow 320. As desired, a fourth temperature sensor 234 can be provided in the measurement interior volume 120 or can be integrated in the gas sensor unit 130, in order to enable a monitoring of the interior temperature $T_I$ in the immediate vicinity of the gas sensor unit 130.

Figure 3:
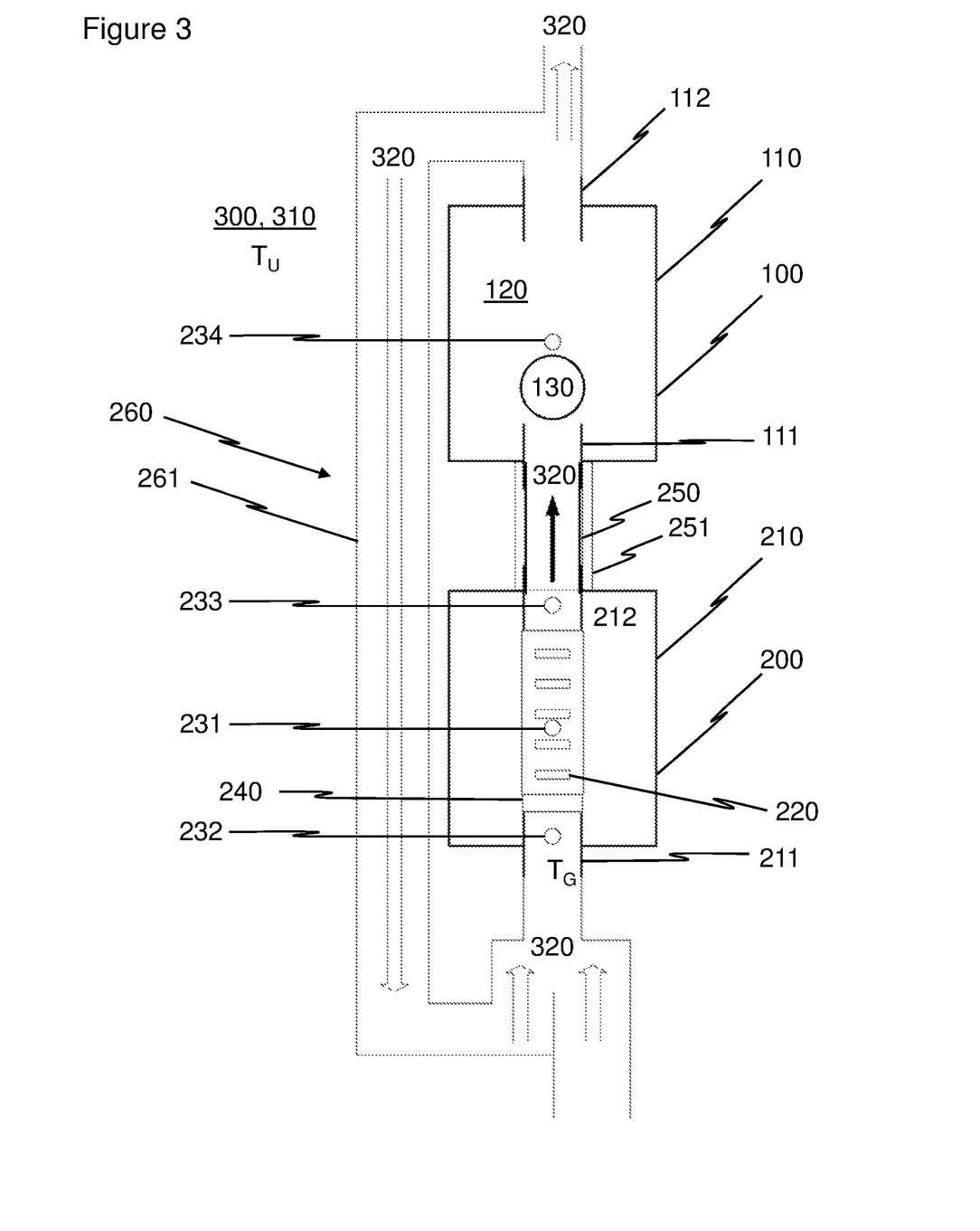

With respect to the second embodiment example, the third embodiment example of a gas measuring device 100 according to the invention according to the diagrammatic representation of FIG. 3, differs by a gas mixture return 260. The gas mixture return 260 comprises a gas mixture return line 261, the input-side end of which is connected in a fluid-conducting manner to the gas outlet 112 of the housing 110 of the gas measuring device 100 and the output-side end of which is connected to the heater housing inlet 211 of the heater housing 210. By means of the gas mixture return line 261, a partial flow of the gas mixture flow 320 flowing out at the gas outlet 112 can be diverted and returned via the heater housing inlet 211 to the heating means 200 and the heating elements 220. The returned partial flow of the gas mixture flow 320 converges at the heater housing inlet 211 with a partial flow of the gas mixture flow 320 coming from the environment 300 and is supplied as mixed flow to the heater housing inlet 211. In the heater housing inlet 211, the second temperature sensor 232 is arranged, wherein, in this embodiment example, the gas inlet temperature $T_G$ measured there has a higher value than the ambient temperature $T_U$. Due to the gas mixture return 260, the total necessary heating power can be reduced. For further reduction, the housing 100, the heater housing 200 and/or the gas mixture return line 261 in each case can optionally be provided with insulation.

Figure 4:
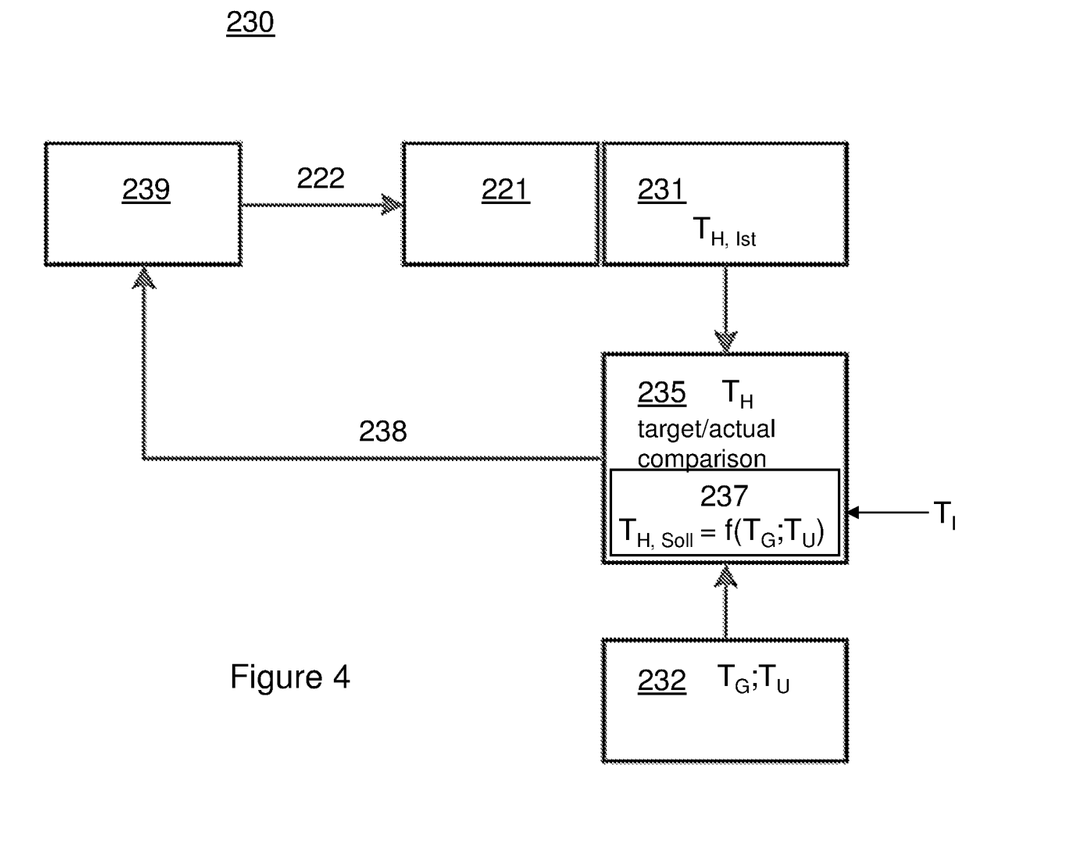

FIG. 4 shows a block diagram of an exemplary control loop of a closed-loop and/or open-loop control system 230 of a heating means 200 according to the invention. Herein, the digital computation unit 235 is connected by signal technology via input-side interfaces to a first temperature sensor 231 for measuring an instantaneous heating temperature $T_H$, Actual and to a second temperature sensor 232 for measuring a gas inlet temperature $T_G$ and/or an ambient temperature $T_U$. The temperature values measured by analog measurement in each case at the temperature sensors 231, 232 are converted by means of an appropriate analog-digital converter and are transmitted to the digital computation unit 235. The computation unit 235 performs a target value/actual value comparison with regard to the heating temperature $T_H$, wherein the target heating temperature $T_{H, Target}$ is computed based on the measured gas inlet temperature $T_G$ and/or the measured ambient temperature $T_U$. For the open-loop and/or closed-loop control of the instantaneous heating temperature $T_{H, Actual}$, the computation unit 235 actuates a heating resistor 221, wherein the output signal digitally output by the computation unit 235 as pulse width modulation 238 is output to a switching power supply 239. Via the heating voltage 222 output by the switching power supply 239 and the heating resistor 221, the heating temperature $T_H$ of the heating element 220 is finally open-loop controlled.

For the indirect open-loop and/or closed-loop control of the interior temperature $T_I$ of the measurement interior volume 120 of the gas measuring device 100 by the represented control loop, in the computation unit 235, in particular on a storage unit 237, a correlation or another relationship between the interior temperature $T_I$ of the measurement interior volume 120 and the instantaneous heating temperature $T_{H, Actual}$ of the at least one heating element 220 and/or an association of concrete values of the instantaneous heating temperature $T_{H, Actual}$ with corresponding values of the interior temperature $T_I$ is stored. A desired interior temperature $T_I$ or a temperature range within which the interior temperature $T_I$ is to be maintained can be stored in the computation unit 235 or stored by a user.

Figure 5:
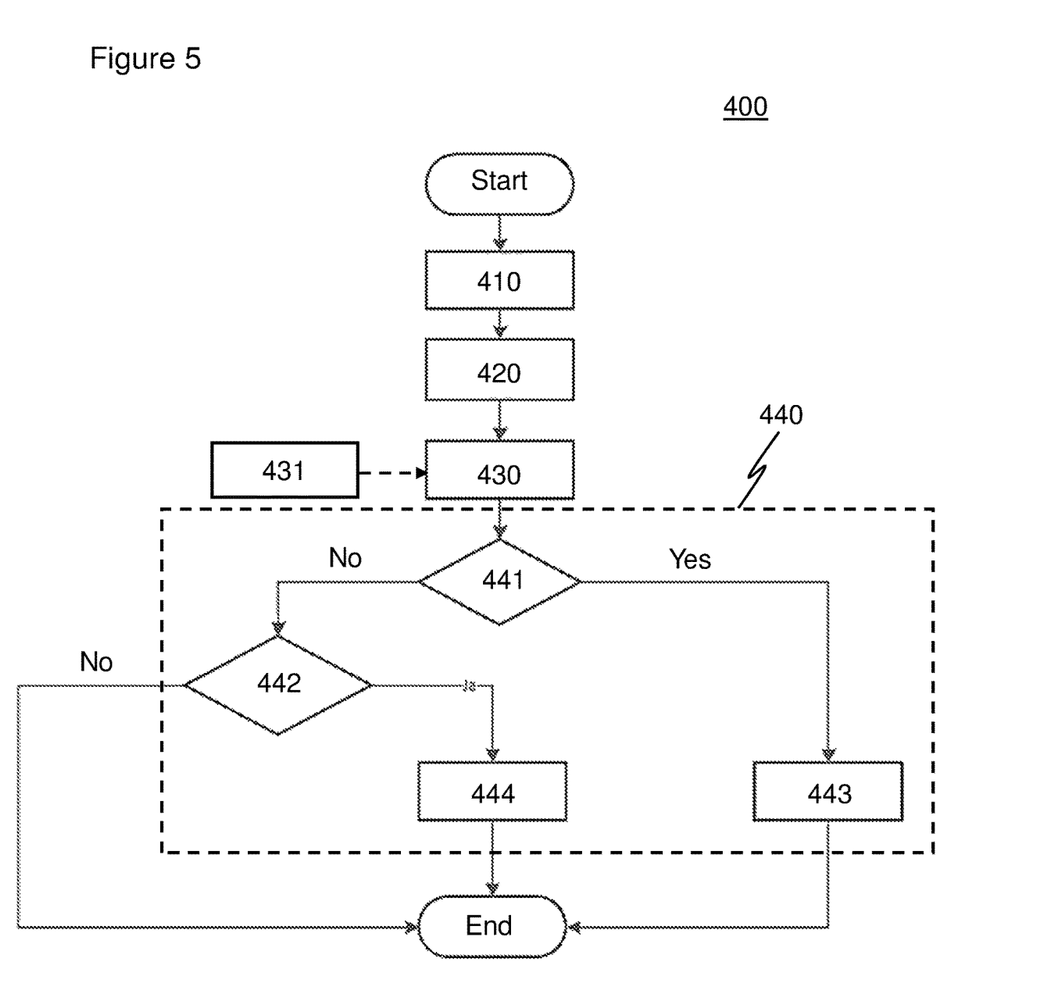

Finally, shown in FIG. 5 is a flow chart of an exemplary sequence of a method according to the invention for open-loop and/or closed-loop control 400 of a heating means 200 with at least one heating element 220 for a gas measuring device 100 (see FIGS. 1-3). With the start of the open-loop and/or closed-loop control method 400, in a first step 410, a gas inlet temperature $T_G$, measured by a second temperature 232 of the heating means 200 and/or a measured ambient temperature $T_U$, is acquired. In a second step 420, an instantaneous heating temperature $T_{H, Actual}$ measured by a first temperature sensor 231 of the heating means 200 is acquired. The first step 410 and the second step 420 as desired can also be carried out successively or also in parallel or simultaneously.

In a third step 430, a target heating temperature $T_{H, Target}$ for the at least one heating element 220 is computed based on the gas inlet temperature $T_G$ measured in the first step 410 and/or the measured ambient temperature $T_U$. For computing the target heating temperature $T_{H, Target}$, in addition to the measured gas inlet temperature $T_G$ and/or the measured ambient temperature $T_U$, a correlation or another relationship between the interior temperature $T_I$ of the measurement interior volume 120 of the gas measuring device 100 and the instantaneous heating temperature $T_{H, Actual}$ of the at least one heating element 220 and/or an association of concrete values of the instantaneous heating temperature $T_{H, Actual}$ with corresponding values of the interior temperature $T_I$ is/are preferably used. Preferably, before the start of the method 400, in a single step 431, the respective correlation or the other relationship and/or the association is/are in particular experimentally determined and stored in the open-loop and/or closed-loop control system 230, in order to be used in additional method runs in the third step 430 in each case for computing the target heating temperature $T_{H, Target}$.

In a fourth step 440, the instantaneous heating temperature $T_{H, Actual}$ is open-loop and/or closed-loop controlled based on the computed target heating temperature $T_{H, Target}$. Here, two successive target value/actual value comparisons 441, 442 are carried out between the instantaneous heating temperature $T_{H,\,Actual}$ and the target heating temperature $T_{H,\,Target}$, wherein, in a first target value/actual value comparison 441, it is checked whether the instantaneous heating temperature $T_{H,\,Actual}$ is less than the target heating temperature $T_{H,\,Target}$. In the case of a positive result of the test (if "Yes"), the at least one heating element 220 is correspondingly actuated, in that a pulse width modulation 238 transmitting the control signal is set "higher" 443, in particular the duty factor of the pulse width modulation 238, that is to say the ratio of the pulse duration to the period duration, is increased. In the case of a negative test result of the first target value/actual value comparison 441 (if "No"), then one continues with a second target value/actual value comparison 442, in which it is checked whether the instantaneous heating temperature $T_{H,\,Actual}$ is higher than the target heating temperature $T_{H,\,Target}$. In the case of a positive result of the test (if "Yes"), the at least one heating element 220 is correspondingly actuated, in that a pulse width modulation 238 transmitting the control signal is set "lower" 444, in particular the duty factor of the pulse width modulation 238 is reduced. In the case of a negative test result of the second target value/actual value comparison 442 (if "No"), the instantaneous heating temperature $T_{H,\,Actual}$ corresponds to the target heating temperature $T_{H,\,Target}$, and the method run is ended without actuation of the at least one heating element 220. Preferably, during the operation of the heating means 200 according to the invention, the described sequence is repeated at regular time intervals.

LIST OF REFERENCE NUMERALS

100 Gas measuring device
110 Housing
111 Gas inlet
112 Gas outlet
120 Measurement interior volume
130 Gas sensor unit
200 Heating means
210 Heater housing
211 Heater housing inlet
212 Heater housing outlet
220 Heating element
221 Heating resistor
222 Heating voltage
230 Open-loop and/or closed-loop control system
231 First temperature sensor
232 Second temperature sensor
233 Third temperature sensor
234 Fourth temperature sensor
235 Digital computation unit
236 Printed circuit board
237 Storage unit
238 Pulse width modulation
239 Switching power supply
240 Fan
250 Pipe connection
251 Insulation
260 Gas mixture return
261 Gas mixture return line
300 Environment
310 Gas mixture
320 Gas mixture flow
400 Open-loop and/or closed-loop control method
410 Acquisition of a gas inlet temperature ($T_G$) and/or of an ambient temperature ($T_U$), first step
420 Acquisition of an instantaneous heating temperature ($T_{H,\,Actual}$), second step
430 Computation of a target heating temperature ($T_{H,\,Target}$), third step
431 Determination of a relationship between the instantaneous heating temperature ($T_{H,\,Actual}$) and the interior temperature ($T_I$)
440 Open-loop control and/or closed-loop control of the instantaneous heating temperature ($T_{H,\,Actual}$), fourth step
441 First target value/actual value comparison
442 Second target/value/actual value comparison
443 Increasing the duty factor
444 Decreasing the duty factor
$T_U$ Ambient temperature
$T_G$ Gas inlet temperature
$T_I$ Interior temperature
$T_V$ Preheating temperature
$T_H$ Heating temperature
$T_{H,\,Actual}$ Instantaneous heating temperature
$T_{H,\,Target}$ Target heating temperature

The invention claimed is:

1. A gas measuring device (100) for analyzing a gas mixture (310) and for monitoring an environment (300), the gas measuring device (100) comprising:
   a housing (110) for delimiting a measurement interior volume (120) or for separating the measurement interior volume (120) from the environment (300) containing the gas mixture (310), the housing (110) having
      a gas inlet (111) and a gas outlet (112) for respective fluid-conducting connection between the measurement interior volume (120) and the environment (300), and
   a gas sensor unit (130), which is arranged within the measurement interior volume (120), for determining a concentration of a gas fraction, contained in the gas mixture (310),
   characterized in that
      the gas measuring device (100) has a heater (200) with at least one heating element (220) and with an open-loop or closed-loop control system (230), wherein, to increase or maintain an interior temperature ($T_I$) of the measurement interior volume (120), a heating temperature ($T_H$) of the at least one heating element (220) is settable by means of the open-loop or closed-loop control system (230), wherein
      the open-loop or closed-loop control system (230) has at least one first temperature sensor (231) for measuring an instantaneous heating temperature ($T_{H,\,Actual}$) of the at least one heating element (220), wherein
      the open-loop or closed-loop control system (230) is an indirect open-loop or closed-loop control of the interior temperature ($T_I$) of the measurement interior volume (120) of the gas measurement device (100), and
      is configured for the open-loop or closed-loop control of the instantaneous heating temperature ($T_{H,Actual}$) on the basis of a presettable target heating temperature ($T_{H,\,Target}$) of the at least one heating element (220),
      by the first temperature sensor (231) being located outside the measurement interior volume (120) and distanced from the gas sensor unit (130).

2. The gas measuring device (100) according to claim 1, characterized in that
   the measurement interior volume (120) and the gas sensor unit (130) are in continuous, fluid-conducting exchange with the environment (300) containing the gas mixture (310), via the gas inlet (111) or the gas outlet (112), for continuous room monitoring.

3. The gas measuring device (100) according to claim 2, characterized in that
the at least one heating element (220) comprises a heating resistor (221) on a radiator, wherein the heating temperature ($T_H$) of the heating element (220) can be open-loop controlled by means of a heating voltage (222) applied to the heating resistor (221).

4. The gas measuring device (100) according to claim 1, characterized in that
the open-loop or closed-loop control system (230) has at least one second temperature sensor (231) for measuring a gas inlet temperature ($T_G$) of the gas mixture (310) present at the gas inlet (111) or an ambient temperature ($T_U$) of the gas mixture (310) present in the environment (300), and the presettable target heating temperature ($T_{H,\ Target}$) can be determined, in each case depending on the measured gas inlet temperature ($T_G$) or the measured ambient temperature ($T_U$)
on the basis of a correlation stored in the open-loop or closed-loop control system (230), between the interior temperature ($T_I$) of the measurement interior volume (120) and the instantaneous heating temperature ($T_{H,\ Actual}$) of the at least one heating element (220) or
on the basis of an association, stored in the open-loop or closed-loop control system (230), of concrete values of the instantaneous heating temperature ($T_{H,\ Actual}$) with corresponding values of the interior temperature ($T_I$).

5. The gas measuring device (100) according to claim 4, characterized in that
the open-loop or closed-loop system (230) of the heater (200) has a digital computation unit (235) which has interfaces with the at least one first temperature sensor (231), with the at least one second temperature sensor (232) and with the at least one heating element (220), and wherein the correlation between the interior temperature ($T_I$) of the measurement interior volume (120) and the instantaneous heating temperature ($T_{H,\ Actual}$) of the at least one heating element (220) or the association of concrete values of the instantaneous heating temperature ($T_{H,Actual}$) with corresponding values of the interior temperature ($T_I$) is or are stored in the computation unit (235), and the computation unit (235) is configured for determining the presettable target heating temperature ($T_{H,\ Target}$) depending on the measured gas inlet temperature ($T_G$) or the measured ambient temperature ($T_U$).

6. The gas measuring device (100) according to claim 5, characterized in that
the digital computation unit (235) is configured for outputting an error message or for switching off the heater (200) if a measured value of the instantaneous heating temperature ($T_{H,\ Actual}$) is less than the temperature minimum reference value stored in the computation unit (235), or the measured value of the instantaneous heating temperature ($T_{H,\ Actual}$) is greater than a stored temperature maximum reference value.

7. The gas measuring device (100) according to claim 1, characterized in that
the gas measuring device (100) comprises a gas mixture return (260) with a gas mixture return line (261), wherein gas mixture (310) flowing out at the gas outlet (112) of the housing (110) can be at least partially supplied via the gas mixture return line (261) to the heating means (200).

8. The gas measuring device (100) according to claim 2, characterized in that
the heater (200) has a fan (240) for generating a gas mixture flow (320).

9. The gas measuring device (100) according to claim 5, characterized in that
the digital computation unit (235) is configured to increase or maintain the interior temperature ($T_I$) of the measurement interior volume (120) of the gas measuring device (100) indirectly by heating a gas mixture flow (320) by the at least one heating element (220).

10. The gas measuring device (100) according to claim 3, characterized in that
the heater (200) has a heater housing (210) for accommodating the at least one heating element (220) and for accommodating the open-loop or closed-loop control system (230), with a heater housing inlet (211) for fluid-conducting connection to the environment (300) and a heater housing outlet (212) for fluid-conducting connection with the gas inlet (111) of the housing (110) of the gas measuring device (100).

11. A heater (200) for a gas measuring device (100) for increasing or maintaining an interior temperature ($T_I$) of a measurement interior volume (120) of the gas measuring device (100), having:
a heater housing (210) with a heater housing inlet (211) for fluid-conducting connection with an environment (300) containing a gas mixture (310) and with a heater housing outlet (212) for fluid-conducting connection with the measurement interior volume (120) of the gas measuring device (100),
at least one heating element (220) which is arranged within the heater housing (210),
an open-loop or closed-loop control system (230) which is arranged within the heater housing (210) and which is configured for setting a heating temperature ($T_H$) of the at least one heating element (220),
characterized in that
the open-loop or closed-loop control system (230)
has at least one first temperature sensor (231) for measuring an instantaneous heating temperature ($T_{H,\ Actual}$) of the at least one heating element (220) and is configured for the open-loop or closed-loop control of the instantaneous heating temperature ($T_{H,\ Actual}$) on the basis of a presettable target heating temperature ($T_{H,\ Target}$) of the at least one heating element (220), and
has at least one second temperature sensor (232) for measuring a gas inlet temperature ($T_G$) of the gas mixture (310) present at the heater housing inlet (211) or for measuring an ambient temperature ($T_U$) of the gas mixture (310) present in the environment (300).

12. The heater according to claim 11, characterized in that
the presettable target heating temperature ($T_{H,\ Target}$) can be determined on the basis of a correlation stored in the open-loop or closed-loop control system (230), between the interior temperature ($T_I$) of the measurement interior volume (120) and the instantaneous heating temperature ($T_{H,\ Actual}$) of the at least one heating element (220) or on the basis of an association, stored in the open-loop or closed-loop control system (230), of concrete values of the instantaneous heating temperature ($T_{H,\ Actual}$) with corresponding values of the interior temperature ($T_I$), in each case depending on the measured gas inlet temperature ($T_G$) or the measured ambient temperature ($T_U$).

13. A method for open-loop or closed-loop control (400) of a heater (200) with at least one heating element (220) for a gas measuring device (100) the method comprising the following steps:
- acquiring (410) a gas inlet temperature ($T_G$) or an ambient temperature ($T_U$), which is measured by means of a first temperature sensor (231),
- acquiring (420) an instantaneous heating temperature ($T_{H,\ Actual}$) of the at least one heating element (220), which is measured by means of a second temperature sensor (232),
- computing (430) a target heating temperature ($T_{H,\ Target}$) for the at least one heating element (220) depending on the measured gas inlet temperature ($T_G$) or the measured ambient temperature ($T_U$),
- open-loop or closed-loop controlling (440) of the instantaneous heating temperature ($T_{H,\ Actual}$) based on the computed target heating temperature ($T_{H,\ Target}$).

14. The method for open-loop or closed-loop control (400) according to claim 13, characterized by open loop controlling the interior temperature ($T_I$) of a measurement interior volume (120) of the gas measuring device (100) by means of the instantaneous heating temperature ($T_{H,\ Actual}$) of the at least one heating element (220), wherein the computation of the target heating temperature ($T_{H,\ Target}$) for the at least one heating element (220) occurs
- based on a correlation between the interior temperature ($T_I$) and the instantaneous heating temperature ($T_{H,\ Actual}$) or
- based on an association of concrete values of the instantaneous heating temperature ($T_{H,\ Actual}$) with corresponding values of the interior temperature ($T_I$).

15. The gas measuring device (100) according to claim 2, characterized in that,
the environment (300) is a room containing the gas mixture and continuously being monitored by the gas measuring device (100), wherein the measurement interior volume (120) and the gas sensor unit (130) are in continuous, fluid-conducting exchange with the room.

16. The gas measuring device (100) according to claim 1, characterized in that,
the gas sensor unit (130) is an electrochemical gas sensor unit for determining an oxygen gas fraction contained in the gas mixture.

* * * * *